United States Patent [19]

Kimura et al.

[11] Patent Number: 5,167,926
[45] Date of Patent: Dec. 1, 1992

[54] APPARATUS FOR PRETREATING CELLS FOR FLOW CYTOMETRY

[75] Inventors: Shiro Kimura, Koganei; Kazuo Miyazawa, Koushoku, both of Japan

[73] Assignee: Kabushiki Kaisha Tiyoda Seisakusho, Koushoku, Japan

[21] Appl. No.: 580,864

[22] Filed: Sep. 11, 1990

[30] Foreign Application Priority Data

Sep. 13, 1989 [JP] Japan .................................. 1-235798

[51] Int. Cl.$^5$ ......................... G01N 9/30; G01N 21/00
[52] U.S. Cl. ........................................ 422/67; 422/64; 422/72; 422/81; 422/100; 436/45; 436/177
[58] Field of Search .................... 422/64, 67, 68.1, 72, 422/81, 100, 101; 436/45, 177

[56] References Cited

U.S. PATENT DOCUMENTS

| | | | |
|---|---|---|---|
| 4,155,978 | 5/1979 | Naono et al. | 422/64 |
| 4,236,666 | 12/1980 | Aeschlimann et al. | 422/72 X |
| 4,323,537 | 4/1982 | Mody | 422/100 X |
| 4,332,768 | 6/1982 | Berglund | 422/100 X |
| 4,708,940 | 11/1987 | Yoshida et al. | 436/45 |
| 4,837,160 | 6/1989 | Meserol et al. | 436/45 |
| 4,845,025 | 7/1989 | Lary et al. | 422/100 X |
| 4,980,130 | 12/1990 | Metzger et al. | 436/177 X |
| 4,983,359 | 1/1991 | Tomioka et al. | 422/81 |

FOREIGN PATENT DOCUMENTS

| | | | |
|---|---|---|---|
| 0192237 | 9/1985 | Japan | 422/81 |
| 2124509 | 2/1985 | United Kingdom | 436/45 |

Primary Examiner—James C. Housel
Assistant Examiner—Arlen Soderquist
Attorney, Agent, or Firm—Ladas & Parry

[57] ABSTRACT

A plurality of open-top sample tubes, each containing a simple liquid containing cells to be treated, are removably mounted on a disklike sample carrier which is rotatable about a vertical axis for centrifuging the samples. Disposed above the sample carrier are a set of fixed reagent supply nozzles for dropping a desired reagent or reagents into the sample tubes and at least one supply-discharge nozzle movable into and out of the successive sample tubes. A hydropneumatic circuit is coupled to the supply-discharge nozzle for intimately intermingling the samples and the reagents and for rinsing the supply-discharge nozzle and other required parts. In an alternate embodiment a single supply-discharge nozzle is employed for reagent supply into the sample tubes, for intermingling the samples and the reagents, and for rinsing.

5 Claims, 14 Drawing Sheets

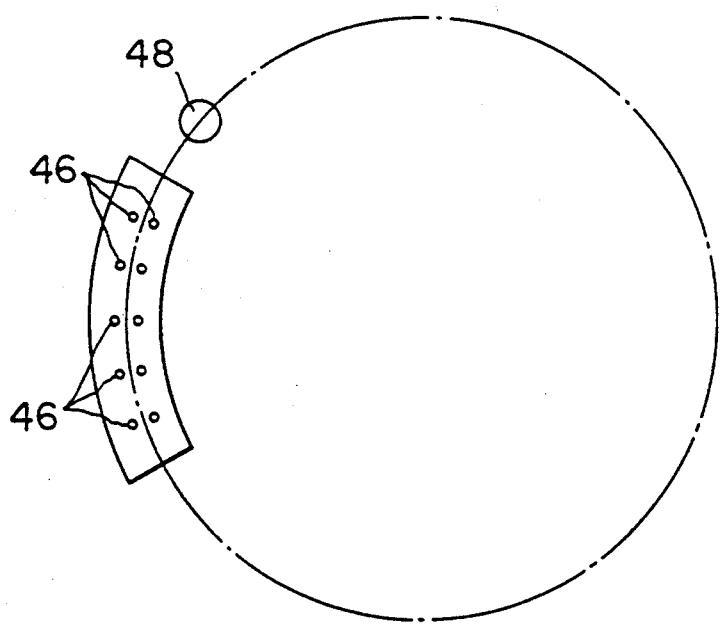
FIG. 4
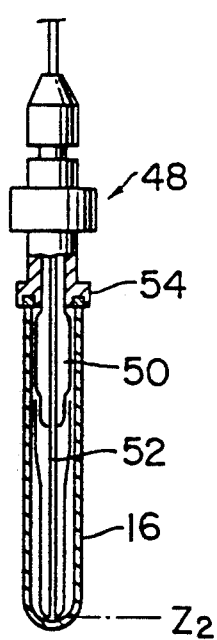
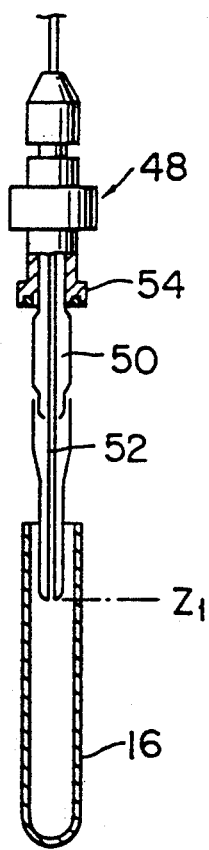
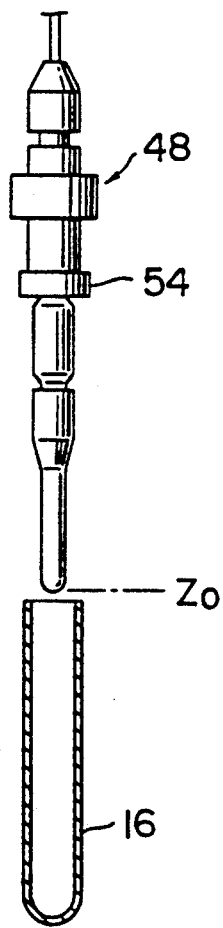
FIG. 5  FIG. 6  FIG. 7

APPARATUS FOR PRETREATING CELLS FOR FLOW CYTOMETRY

BACKGROUND OF THE INVENTION

This invention belongs to the realm of cytology or the study of cells and relates more specifically to an apparatus for the fully automatic and streamlined treatment of cells preparatory to their flow cytometric or like cytological studies. Among such studies are the measurements of individual cell sizes and relative intracellular amounts of deoxyribonucleic acid (DNA).

Flow cytometry represents one of the essential tools employed in such fields as cytologic biology, cellular immunochemistry, and cytodiagnosis for cancer detection. Essentially, it aims at the classification of cells according to their sizes, types, contents of intracellular components, and like characteristics. Flow cytometry involves the pigmentation of cells with fluorescent dyes. The pigmented cells are caused to individually fluorescence under laser beam irradiation while flowing through slender tubing. The intensities of fluorescence of the individual cells are measured for the determination of their sizes, relative amounts of DNA, etc.

One of the problems left unsolved in the art of flow cytometry is how to expedite the complete process of pretreating cells to be studied. Such pretreatment consists of many steps to be followed strictly in a prescribed order. Among the steps are the introduction of reagents into cell samples within sample tubes, the centrifugal treatment of the sample-reagent mixtures, the removal of the unnecessary liquid tops from the sample tubes, the staining of the cells with a fluorescent dye, and the filtration of the samples. The actual process is much more complex.

Conventionally, as far as we are aware, such cell pretreatment has been mostly performed manually at the cost of much time and labor. Manual pretreatment is also undesirable by reasons of unavoidable human errors and the nonuniformity of operations from one individual operator to another. The advent of an apparatus capable of full automation of cell pretreatment has thus been long awaited by the cytologists for the elimination of human toil and for gaining stability and constancy in the operations involved No such apparatus is known to us, however, because of the complexities of the processes of cell pretreatment.

SUMMARY OF THE INVENTION

The present invention seeks to provide an apparatus capable of automatically performing the standard processes of cell treatment preparatory to flow cytometry and like cytological studies in a streamlined manner.

Stated in its simplest form, the cell treating apparatus according to the invention comprises a rotary sample carrier for carrying one or more sample containers, usually in the form of test tubes, for containing a sample liquid including cells to be treated. The sample carrier is rotatable about a vertical axis for centrifuging the sample liquid within the sample containers. Also included is nozzle means for introducing a reagent or reagents and a rinsing liquid into the sample containers on the sample carrier, and a temporary storage vessel capable of communication with the nozzle means. Valve means is provided for controlling the communication of the nozzle means with the sample containers, a reagent container or containers, a rinsing liquid container, a pneumatic energy source means, and the temporary storage vessel in order to intimately intermingle the sample liquid and the reagent by causing the flow of the sample-reagent mixture back and forth between the sample container and the temporary storage vessel, and to rinse the nozzle means and the temporary storage vessel with the rinsing liquid Constant temperature means is also provided for controlling the temperature of the sample liquid within the sample containers on the sample carrier.

In one preferred embodiment of this invention the nozzle means comprises a plurality of reagent supply nozzles for dropping a reagent or reagents into the respective sample containers on the sample carrier, and a supply-discharge nozzle movable into and out of the successive sample containers for introducing the rinsing liquid therein, and for withdrawing the rinsing liquid, and the sample-reagent mixture therefrom, under the force of the pneumatic energy. Alternatively, a plurality of supply-discharge nozzles, and as many temporary storage vessels, may be provided one for each sample container for simultaneously processing all the samples within the sample containers.

In another preferred embodiment the nozzle means comprises only a supply-discharge nozzle in combination with a rotary selector valve in communication with both reagent containers and a rinsing liquid container. The supply-discharge nozzle is utilized for reagent supply into the successive sample tubes, for intermingling the samples and the reagents, and for rinsing. Here again a plurality of supply-discharge nozzles may be provided for the concurrent treatment of all the samples within the sample containers.

Constructed as in the foregoing, the apparatus of this invention can automatically perform all the required steps of cell pretreatment in a prescribed sequence. Such automatic, streamlined cell pretreatment under unvarying conditions is believed to materially enhance the reliability of the subsequent cytodiagnosis and other examinations by flow cytometry.

The above and other features and advantages of this invention and the manner of realizing them will become more apparent, and the invention itself will best be understood, from a study of the following description and appended claims, with reference had to the attached drawings showing some preferred embodiments of the invention.

BRIEF DESCRIPTION OF THE DRAWINGS

FIG. 4 is a top plan of the reagent supply nozzles and the air-liquid supply-discharge nozzle of the cell treating apparatus, seen in the direction of the arrows IV in FIG. 2;

FIG. 5 is a side elevation, partly shown in axial section for clarity, of the supply-discharge nozzle shown in a preassigned lowermost position for full insertion in one of the sample tubes on the sample carrier;

FIG. 6 is a view similar to FIG. 5 except that the supply-discharge nozzle is shown in a preassigned intermediate position for partial insertion in one of the sample tubes;

FIG. 7 is also a view similar to FIG. 5 except that the supply-discharge nozzle is shown in a preassigned uppermost position for withdrawal from the sample tube.

DESCRIPTION OF THE PREFERRED EMBODIMENTS

Figure 1:
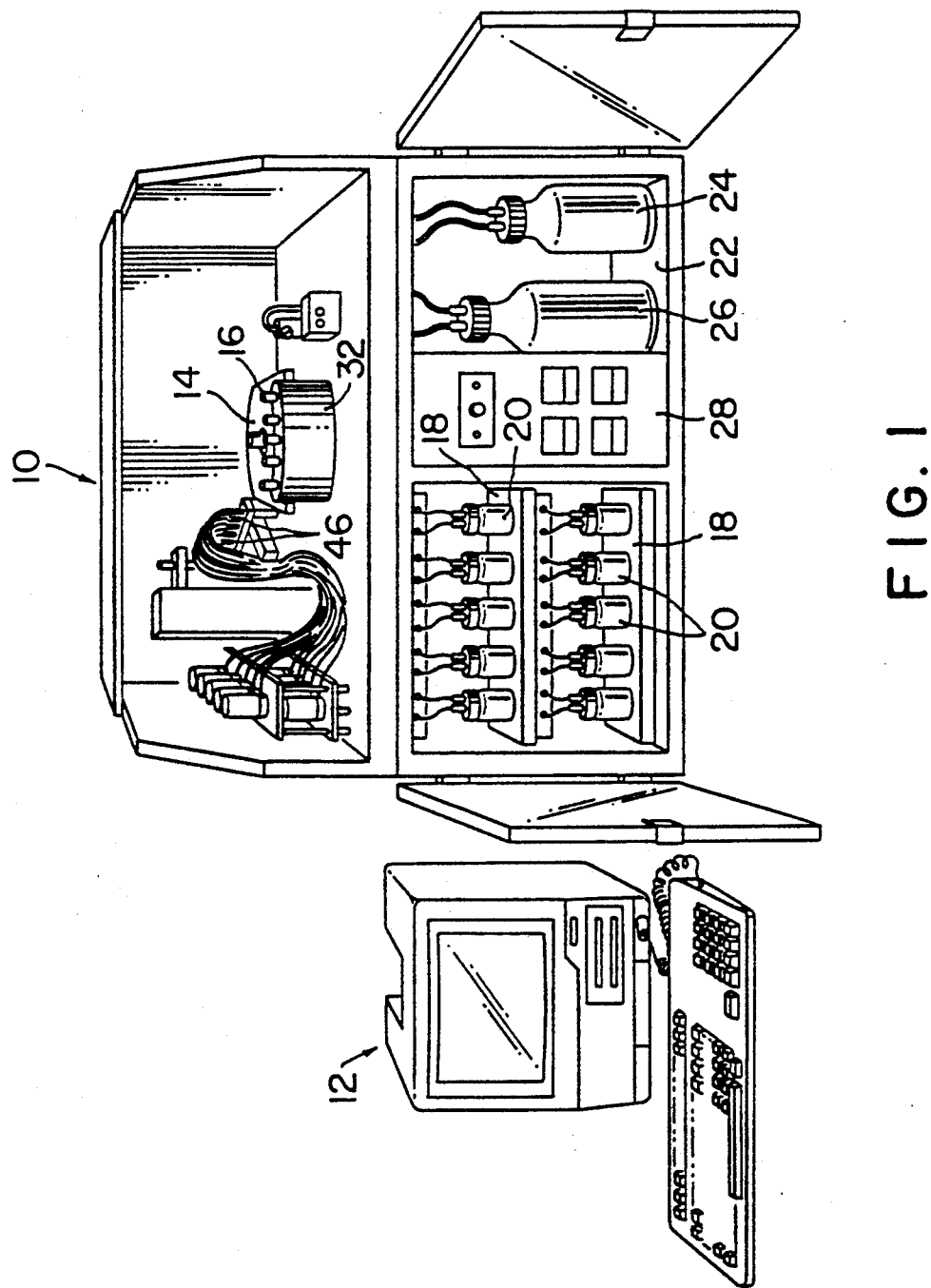
FIG. 1 is a perspective view of the cell treating apparatus embodying the principles of this invention.

The cell treating apparatus embodying the present invention is generally designated 10 in FIG. 1 and therein shown together with an electronic computer system 12 for fully automating its operation. The cell treating apparatus 10 includes a rotary sample carrier 14 rotatably mounted in an upper section of the apparatus. The rotary sample carrier 14 peripherally carries one or more open-top sample containers 16 in which are to be received liquid samples including cells to be processed. The sample containers 16 are shown as test tubes.

Disposed in a lower section of the apparatus 10 and on one side thereof are reagent racks 18 for holding a set of reagent bottles or containers 20. On the other side there is formed a chamber 22 for accommodating a rinsing liquid reservoir 24 and a waste liquid reservoir 26. Both reservoirs 24 and 26 are shown as bottles. A temperature control panel 28 is provided in the middle of the lower section.

Figure 2:
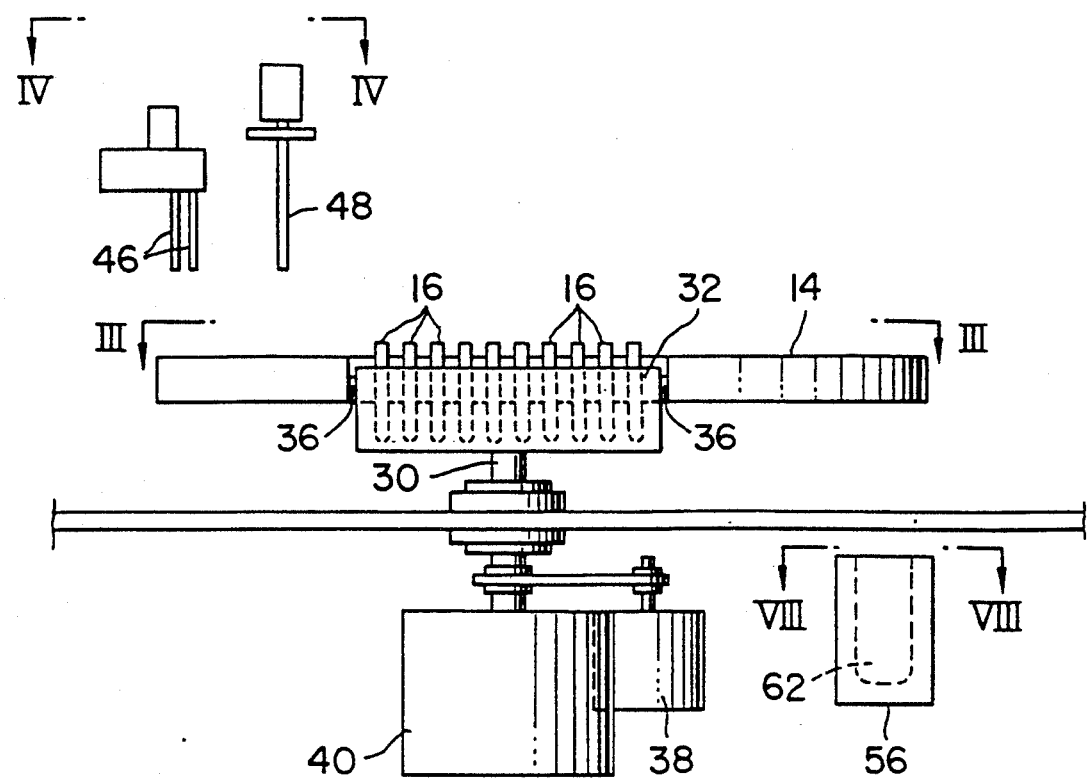
FIG. 2 is a diagrammatic side elevation of some important parts and components o the cell treating apparatus.
Figure 3:
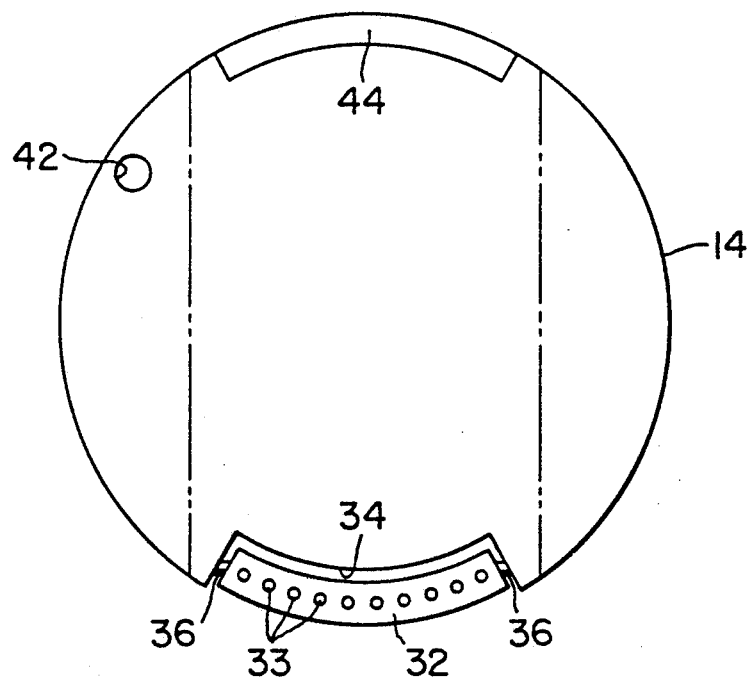
FIG. 3 is a top plan of the rotary sample carrier of the cell treating apparatus, seen in the direction of the arrows III in FIG. 2.

As shown in greater detail in FIGS. 2 and 3, the rotary sample carrier 14 takes the form of a disk in this particular embodiment. The disk is mounted on an upstanding drive spindle 30 for joint rotation therewith. A sample rack 32 for removably holding the open-top sample containers or tubes 16 in a row is swingably mounted to the sample carrier 14 so as to extend along part of its periphery. Arcuate in shape as seen in a plan view as in FIG. 3, the sample rack 32 has a row of holes 33 formed therethrough in arcuate arrangement for receiving the sample tubes 16. The sample rack 32 is received with clearances in a peripheral recess 34 in the sample carrier 14 and has its opposite extremities coupled to the sample carrier via a pair of trunnions 36 for swinging movement about the same.

FIG. 2 shows two electric drive motors 38 and 40 to be selectively coupled as via an electromagnetic clutch, not shown, to the drive spindle 30. The first drive motor 38 is for driving the sample carrier 14 at sufficiently high speed for centrifugal treatment of the samples within the sample tubes 16. The second drive motor 40 is for driving the sample carrier 14 at lower speed for positioning purposes. Therefore, hereinafter in this specification, the first drive motor 38 will be referred to as the centrifuge motor, and the second drive motor 40 as the positioning motor, by way of contradistinction from each other.

Seen at 42 in FIG. 3 is an opening formed through the sample carrier 14 in a prescribed angular position adjacent the disk periphery for a purpose yet to be described. This opening would be unnecessary, however, if the sample carrier were shaped as indicated by the broken lines in FIG. 3.

As has been mentioned with reference to FIG. 3, the sample rack 32 is swingably mounted to the sample carrier 14 via the trunnions 36. The sample tubes 16 are held in an upstanding attitude when the sample carrier 14 is at rest. When the sample carrier 14 is driven at high speed by the centrifuge motor 38, on the other hand, the lower parts of the sample tubes 16 will be centrifugally flung radially outwardly of the sample carrier, so that the sample liquid will not spill over the sample tubes. A counterweight 44 may be attached as required to the sample carrier 14 in a position diametrically opposite to the sample rack 32 in order to prevent the possible wobbling of the sample carrier during high speed rotation.

Both FIGS. 2 and 4 indicate a plurality of reagent supply nozzles 46 and a single air-liquid supply-discharge nozzle 48, both disposed over the circular path of the sample tubes 16 on the sample rack 32. The reagent supply nozzles 46 are for dropping a reagent or reagents into the sample tubes 16. Preferably, there may be provided as many reagent supply nozzles 46 as the expected maximum number of different kinds of reagents to be employed in various cell pretreatment processes. However, in the simplest form of cell treating apparatus according to this invention, only one reagent supply nozzle may be provided for dropping a reagent or reagents into one or more sample tubes on the sample rack 32.

As illustrated on an enlarged scale in FIGS. 5–7, the air-liquid supply-discharge nozzle 48 is intended for the delivery and discharge of both air under pressure and liquid into and from the sample tubes 16. A suitable linear drive means such as that comprising a worm-and-nut assembly or a linear actuator, not shown, is coupled to the air-liquid supply-discharge nozzle 48. Driven by any such means, the supply-discharge nozzle 48 is to be selectively moved to any of a lowermost position $Z_2$, FIG. 5, an intermediate position $Z_1$, FIG. 6, and an uppermost position $Z_0$, FIG. 7. The supply-discharge nozzle 48 is fully received in one of the sample tubes 16 when in the lowermost position $Z_2$, partly received therein when in the intermediate position $Z_1$, and fully withdrawn therefrom when in the uppermost position $Z_0$.

FIG. 5 clearly reveals an air passageway 50 and a liquid passageway 52 extending coaxially through the supply-discharge nozzle 48. A flange 54 on the nozzle 48 functions as a cap for hermetically closing the open top of any selected one of the sample tubes 16 when the nozzle is in the lowermost position $Z_2$ as in FIG. 5.

Figure 8:
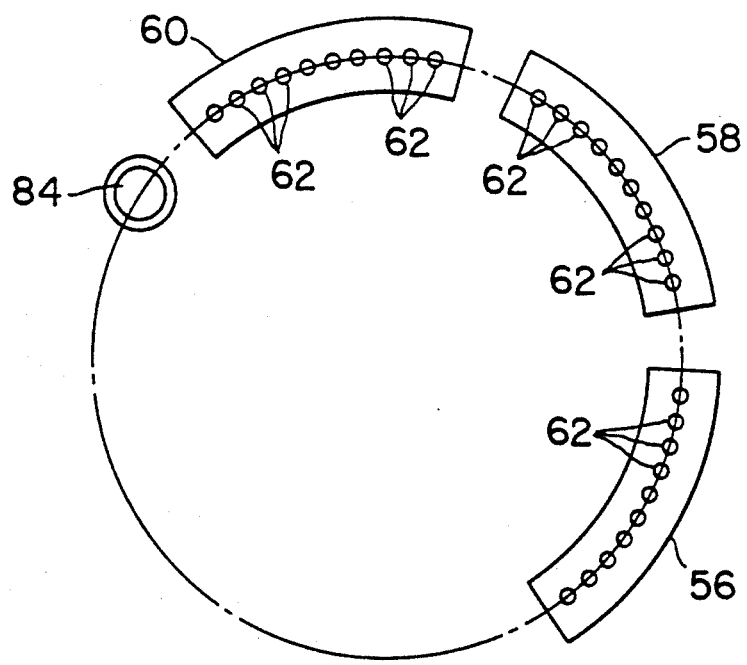
FIG. 8 is a top plan of the constant temperature vessels of the cell treating apparatus, seen in the direction of the arrows VIII in FIG. 2.

As will be understood from both FIGS. 2 and 8, three constant temperature vessels 56, 58 and 60 are provided in a row under the rotary sample carrier 14 and along the circular path of the sample tubes 16 being carried thereby. Typically, each constant temperature vessel takes the form of a block of aluminum with a row of holes 62 defined vertically downwardly from its top. The row of holes 62 are arranged arcuately about the axis of the sample carrier 14 and at the same pitch as the row of holes 33, FIG. 3, in the sample rack 32. The constant temperature vessels 56, 58 and 60 are movable up and down with respect to the sample carrier 14.

Normally, the three constant temperature vessels 56, 58 and 60 are held lowered in the position of FIG. 2. The sample tubes 16 on the sample rack 32 can be brought into vertical register with the set of holes 62 in any of the three constant temperature vessels 56–60 with the rotation of the sample carrier 14. Then the desired vessel may be raised for receiving lower parts of the sample tubes 16 in its holes 62.

In practice, the three constant temperature vessels 56, 58 and 60 may be held at constant temperature of, for example, 4°, 40° and 30° C., respectively. The temperatures of the aluminum blocks constituting the constant temperature vessels may be maintained at these values thermostatically. Also, as required, suitable air passageways may be cut in the sample rack 32, and air of desired temperatures may be applied through such passageways to the sample tubes 16 for more efficiently heating or cooling the reagents or other substances contained therein.

FIGS. 9 through 13 diagrammatically illustrate, in various stages of operation, a hydropneumatic circuit 63 for use as in intermingling the samples and reagents and in rinsing, the sample tubes 16 and other parts. It will be noted that the circuit includes the air-liquid supply-discharge nozzle 48 which is shown in FIGS. 9–12 fully inserted in one of the sample tubes 16. The air passageway 50 in the supply-discharge nozzle 48 is to be placed in and out of communication with a source 64 of air under pressure and with atmosphere (FIGS. 10 and 11) by a three-way directional-control valve 66. The liquid passageway 52 in the supply-discharge nozzle 48 is to be placed in and out of communication with one of the two inlet-outlet ports of a temporary storage vessel 68 by another three-way valve 70.

Figure 13:
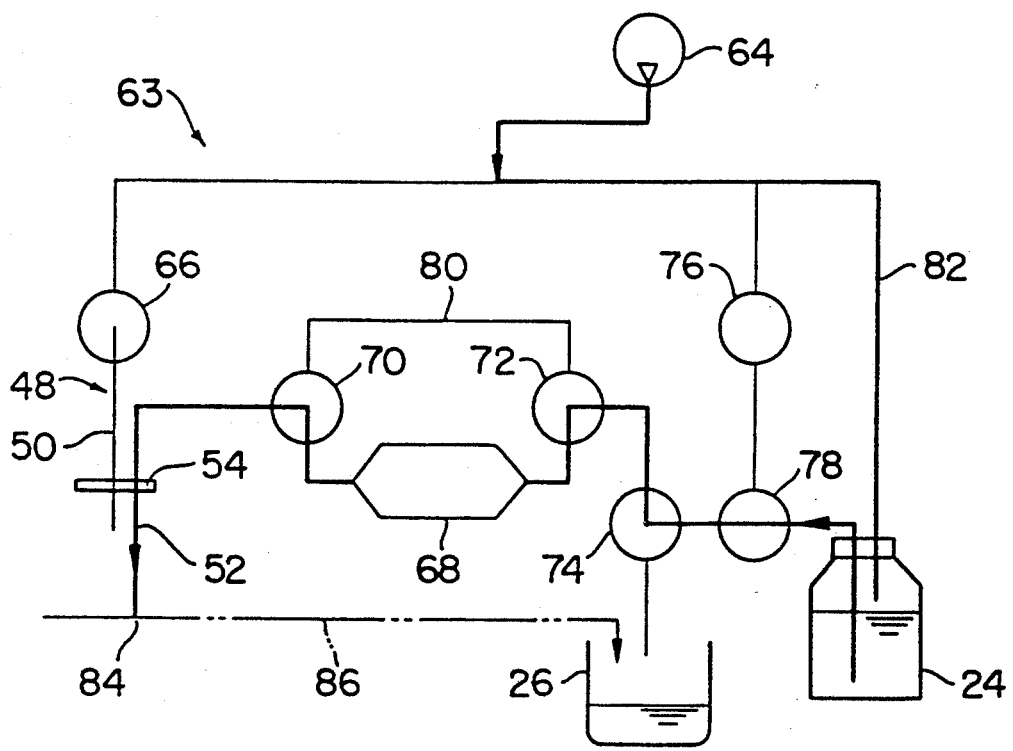

The other inlet-outlet port of the temporary storage vessel 68 is to be placed in and out of selective communication with either the waste liquid reservoir 26 (FIG. 9), the pressurized air source 64 (FIG. 10), or the rinsing liquid reservoir 24 (FIG. 13) by three additional three-way valves 72, 74 and 78 and an on-off valve 76. A bypass conduit 80 extends between the valves 70 and 72, bypassing the temporary storage vessel 68. An additional conduit is provided at 82 for directly communicating the pressurized air source 64 with the headspace within the rinsing liquid reservoir 24 (FIGS. 11 and 13).

Operation

The operation of the apparatus 10 will now be described in terms of how cells are processed preparatory to flow cytometry. Liquid samples containing the cells to be pretreated are charged into the sample tubes 16. These tubes may then be inserted in the holes 33 in the sample rack 32 on the sample carrier 14.

Figure 14:
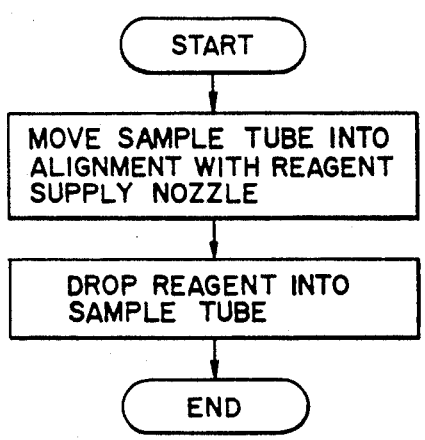
FIG. 14 is a flowchart of a reagent introduction routine in the automatic operation of the cell treating apparatus.

A primary step in cell pretreatment is the introduction of a fluorescent dye or like reagent into the sample tubes 16. FIG. 14 gives a flowchart of this reagent introduction routine. First, the sample carrier 14 is revolved by the positioning motor 40 to bring the sample tubes 16 into alignment with the reagent supply nozzles 46. Then a fluorescent dye or the like is dropped from these nozzles into the sample tubes 16.

Figure 15:
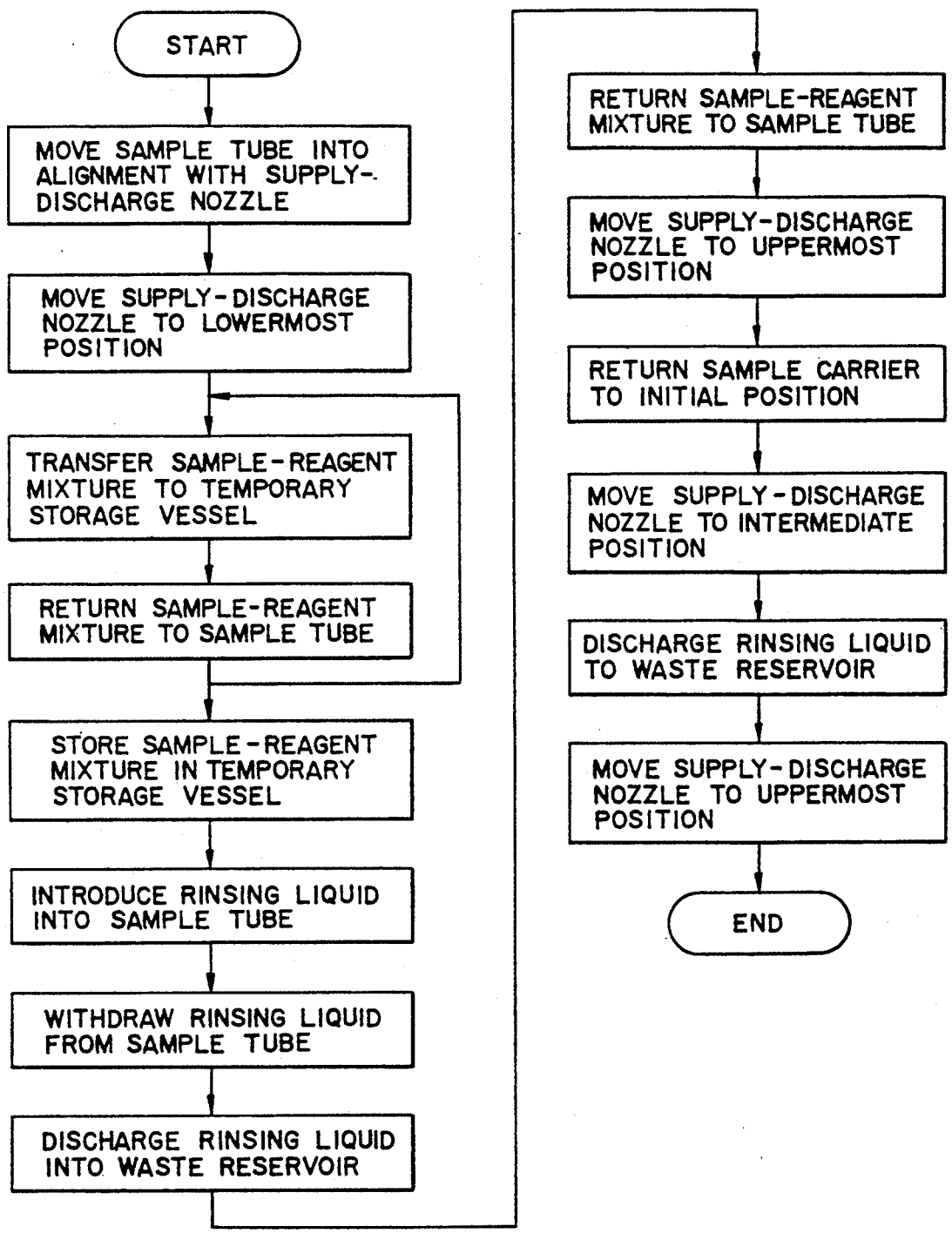
FIG. 15 is a flowchart of an intermingling and rinsing routine in the automatic operation of the cell treating apparatus.

The next step is the intimate intermingling of the samples and the reagent, followed by the rinsing of the sample tubes 16 and other required parts of the hydropneumatic circuit 63, through the procedure flowcharted in FIG. 15. One of the sample tubes 16 on the sample carrier 14, containing both the sample liquid and the reagent, may first be brought into vertical alignment with the air-liquid supply-discharge nozzle 48 by revolving the sample carrier with the positioning motor 40. Then the supply-discharge nozzle 48 may be lowered to the lowermost position $Z_2$. As will be seen by referring again to FIG. 5, the supply-discharge nozzle 48 when in this lowermost position $Z_2$ is fully received in one of the sample tubes 16, hermetically closing that sample tube with the nozzle flange 54.

Figure 9:
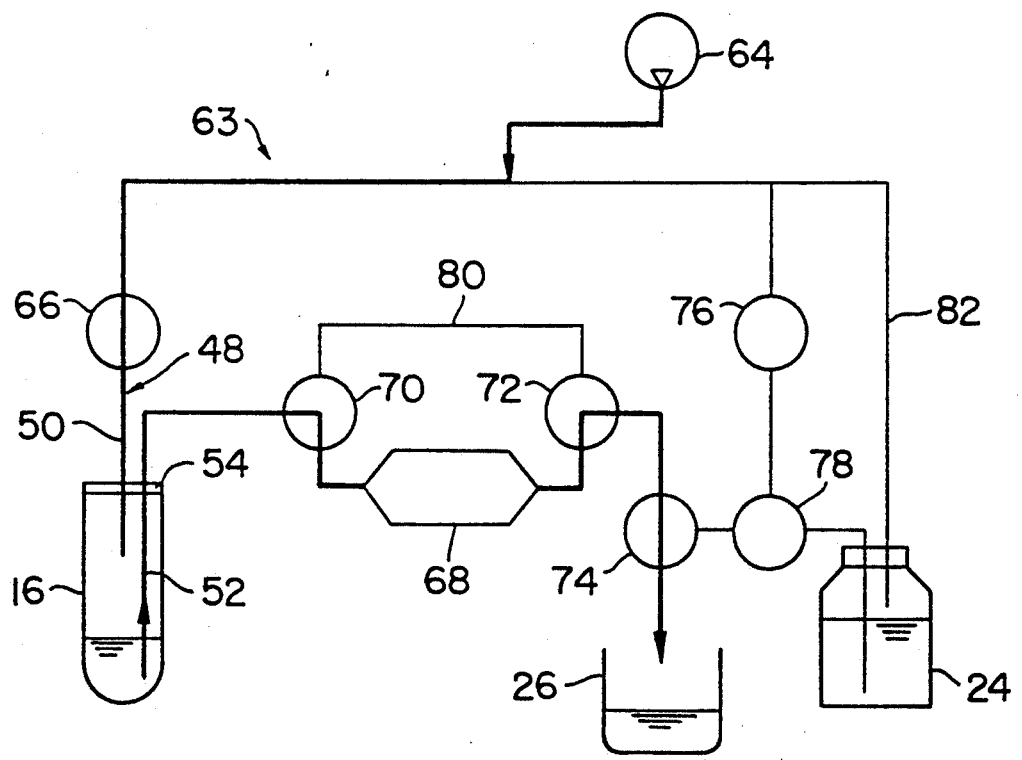
FIGS. 9 through 13 is a series of diagrams showing the hydropneumatic circuit of the cell treating apparatus in various stages of cell treatment.

Then, as shown in the diagram of FIG. 9, air under pressure is directed from the source 64 into the sample tube 16 through the valve 66 and the air passageway 50 in the supply-discharge nozzle 48. Since the sample tube 16 is now hermetically closed as aforesaid, the sample-reagent mixture will be pneumatically forced out therefrom into the temporary storage vessel 68 via the valve 70. The valve 66 is closed immediately upon completion of delivery of the sample-reagent mixture from sample tube 16 to storage vessel 68. It is recommended that a suitable sensor, not shown, be provided for sensing such full delivery of the mixture from sample tube 16 to storage vessel 68.

Figure 10:
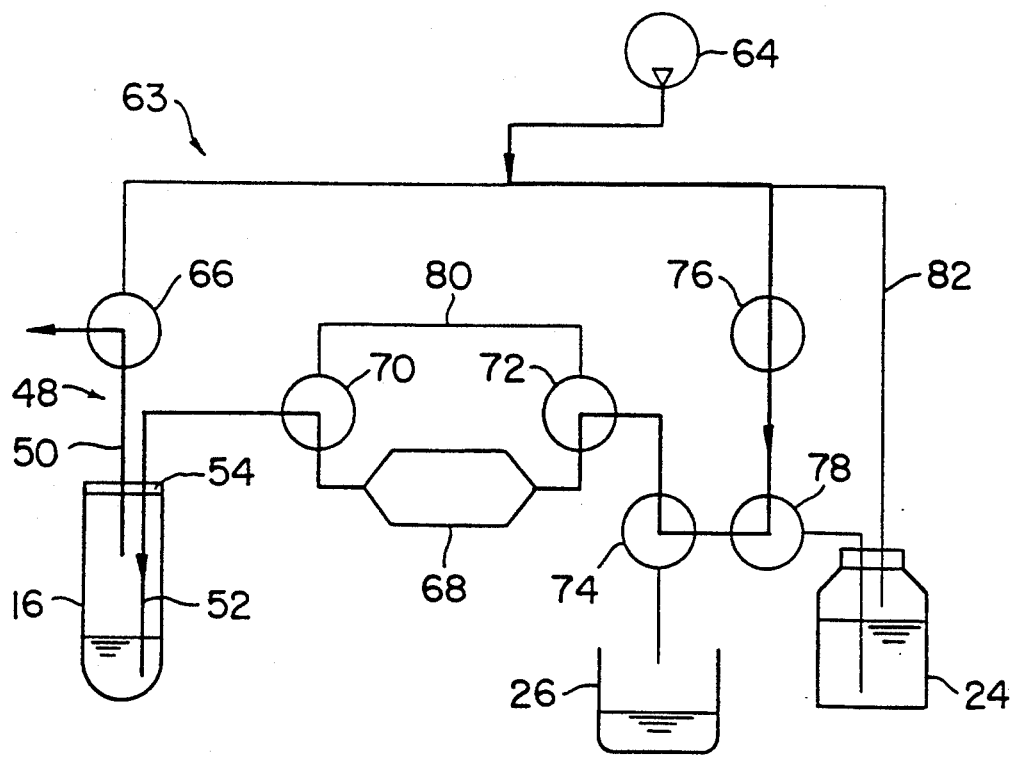
Figure 11:
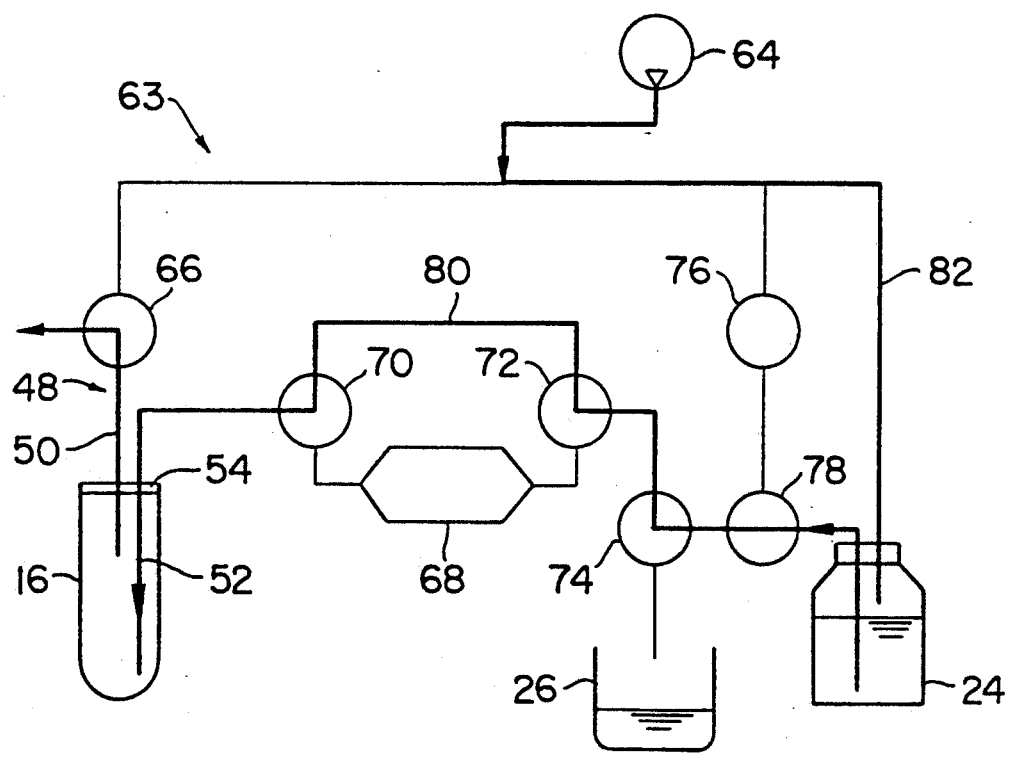

Then pressurized air is directed from the source 64 into the storage vessel 68 through the valves 76, 78, 74 and 72, as illustrated in FIG. 10. It is understood that the valve 70 holds the storage vessel 68 in communication with the sample tube 16, and the valve 66 holds the sample tube in communication with atmosphere, during such air delivery into the storage vessel 68. Accordingly, the sample-reagent mixture will return from storage vessel 68 into sample tube 16. Such flow of the sample-reagent mixture back and forth between sample tube 16 and storage vessel 68 may be repeated a required number of times for fully intermingling the sample and the reagent.

Some cell pretreatment methods require the mechanical agitation of the sample-reagent mixture within each sample tube. To this end a set of agitator rods, each shaped like a poppet valve, may be provided above the sample carrier 14 for up and down movement into and out of the sample tubes.

Following the completion of the full intermingling of the sample and the reagent, the supply-discharge nozzle 48, storage vessel 68 and any other part of the hydropneumatic circuit 63 that has been exposed to the sample and the reagent during their intermingling must be rinsed preparatory to the next step of sample treatment.

Let us assume that the sample-reagent mixture is now contained in the storage vessel 68 as in FIG. 9. Then all the valves 66, 70, 72, 74, 76 and 78 of the hydropneumatic circuit 63 will be actuated to the positions depicted in FIG. 11. Then air under pressure will be fed from the source 64 into the rinsing liquid reservoir 24 through the conduit 82. Since this reservoir 24 is assumed to be closed hermetically, the rinsing liquid will be pneumatically forced out therefrom into the empty sample tube 16 through the bypass conduit 80 around the storage vessel 68.

Figure 12:
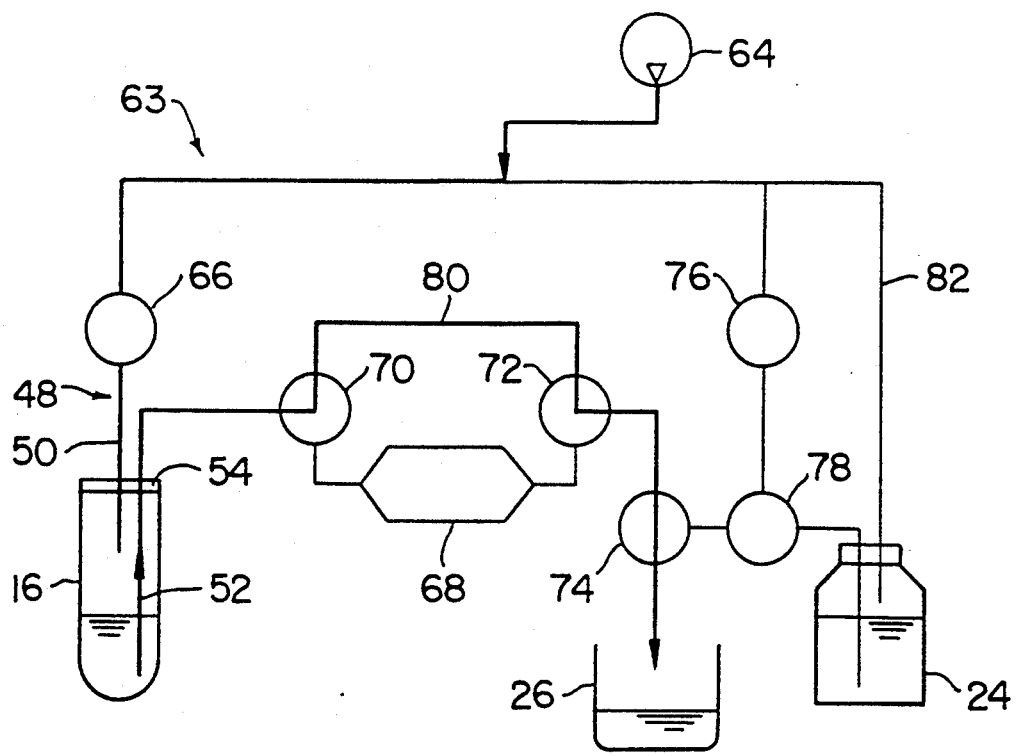

Then all the valves of the hydropneumatic circuit 63 will be actuated to the positions of FIG. 12. Then air under pressure will be charged into the sample tube 16 through the valve 66. The rinsing liquid that has been filled in the sample tube 16 will then be discharged therefrom and made to flow into the waste liquid reservoir 26 through the bypass conduit 80.

With the rinsing of the supply-discharge nozzle 48 completed as above, the valves are actuated to the positions of FIG. 10. Then air under pressure will be fed from the source 64 into the storage vessel 68 through the valves 76, 78, 74 and 72. The sample-reagent mixture will then be forced back into the sample tube 16.

Then the supply-discharge nozzle 48 is raised to the uppermost position $Z_0$, FIG. 7, in which the nozzle is fully withdrawn from the sample tube 16. Then the positioning motor 40 is energized to revolve the sample carrier 14 back to the initial position where the hole 42, FIG. 3, in the sample carrier is in vertical alignment with a discharge port 84, FIG. 8, disposed under the supply-discharge nozzle 48. As illustrated in FIG. 13, the discharge port 84 communicates with the waste liquid reservoir 26 via a conduit or other passageway 86. Then the supply-discharge nozzle 48 is lowered to the intermediate position Z, FIG. 6, in which the nozzle communicates directly with the discharge port 84.

Then all the valves of the hydropneumatic circuit are actuated to the positions of FIG. 13. Then air under pressure is introduced from the source 64 into the rinsing liquid reservoir 24 via the conduit 82. Driven by the pressurized air, the rinsing liquid will flow from the reservoir 24 into the storage vessel 68 via the valves 78, 74 and 72 and thence into the waste liquid reservoir 26 via the valve 70, supply-discharge nozzle 48 and passageway 86.

Then the supply-discharge nozzle 48 is raised from intermediate position $Z_1$, FIG. 6, to uppermost position $Z_0$, FIG. 7, in which latter position the nozzle is fully withdrawn from the hole 42 in the sample carrier 14. Now have been completed the intermingling of the samples and the reagent within the sample tubes 16 and the subsequent rinsing of the necessary parts of the hydropneumatic circuit 63 in accordance with the flowchart of FIG. 15.

The next step is the centrifugal treatment of the samples within the sample tubes 16. To this end the drive spindle 30 of the sample carrier 14 is coupled to the centrifuge motor 38 via the unshown clutch. Then the centrifuge motor 38 is energized to revolve the sample carrier 14 at sufficiently high speed for the desired centrifugal treatment of the samples within the sample tubes 16. Then the supply-discharge nozzle 48 is inserted in the successive sample tubes 16 for withdrawing and discharging unnecessary liquid tops of their contents.

Figure 16:
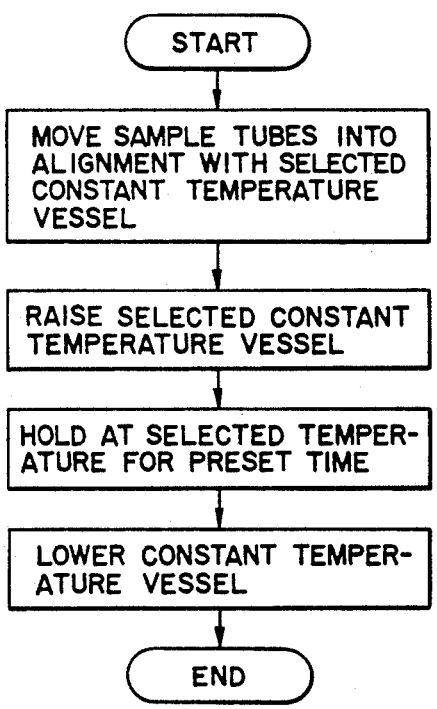
FIG. 16 is a flowchart of a temperature control routine in the automatic operation of the cell treating apparatus.

The next step is the heat treatment of the samples. The flowchart of FIG. 16 may be followed for such heat treatment.

Figure 17:
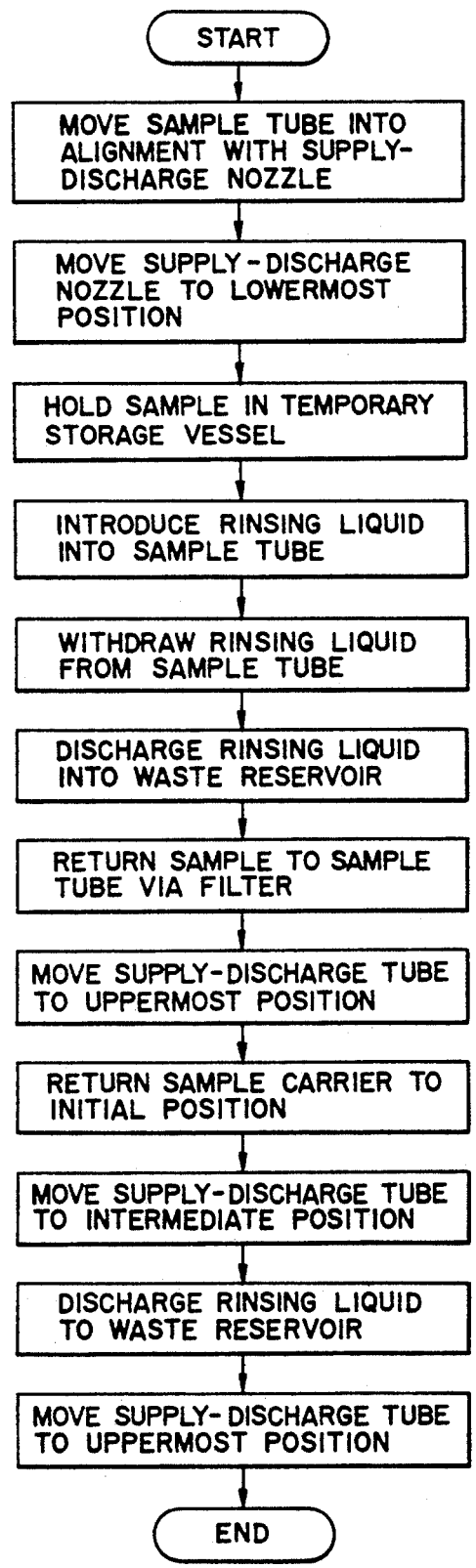
FIG. 17 is a flowchart of a filtration and rinsing routine in the automatic operation of the cell treating apparatus.

Then the samples are put to the filtration routine flowcharted in FIG. 17. The filtration routine is intended for the removal of any foreign matter or impurities that may be contained in the samples, including tissues or coherent aggregates of cells that are not fit for flow cytometry.

The filtration routine involves, first of all, the transfer of the sample from each sample tube 16 to the storage vessel 68 via a sample filter, not shown in this embodiment, provided between supply-discharge nozzle 48 and valve 70. The various valves of the hydropneumatic circuit is set in the positions of FIG. 9 for such sample transfer and consequent filtration. Then, with the valves actuated to the positions of FIG. 11, the rinsing liquid is pneumatically forced from the reservoir 24 into the sample tube 16 thereby washing the unshown sample filter free of the solids that have been removed from the sample liquid. Then the valves are actuated to the positions of FIG. 12, and the rinsing liquid containing the solids is pneumatically withdrawn from the sample tube 16 and discharged into the waste reservoir 26. Then the valves are actuated to the positions of FIG. 10, and the sample liquid is pneumatically returned to the sample tube 16.

The filtration of the sample liquid has now been completed. Subsequently, the supply-discharge nozzle 48 and storage vessel 68 are rinsed with the liquid from the reservoir 24. These parts can be rinsed in the same manner as after the intermingling of the sample liquid and the reagent, as will be understood from the flowchart of FIG. 17 taken together with FIG. 13.

The above described process of cell pretreatment is to be performed for each of the sample tubes 16 on the sample carrier 14. Toward this end the sample carrier 14 is indexed by the positioning motor 40 to bring the successive sample tubes 16 into register with the supply-discharge nozzle 48. The sample tubes containing the pretreated samples are unloaded from the apparatus 10 and transferred to separate equipment for flow cytometry.

As has been mentioned, only one reagent supply nozzle may be provided for dropping a reagent into one or more sample tubes 16 on the sample carrier 14. However, in cases where two or more sample tubes are loaded on the sample carrier 14, the dropping of a reagent into the successive sample tubes from the same supply nozzle may be undesirable because of the differences in reaction time among the samples. A plurality of reagent supply nozzles may therefore be provided as in the apparatus 10 disclosed above. Any desired reagent may be introduced simultaneously from such supply nozzles into all the same tubes on the same carrier 14 if the reaction time is desired to be the same for all the samples.

Similarly, there may be provided as many supply-discharge nozzles 48, and as many storage vessels 68 capable of communication with each such nozzle, as there are sample tubes 16 to be processed simultaneously. All the samples within the sample tubes 16 will then be treated concurrently, instead of one after another as in the foregoing description of operation.

Some reagents for use in cell pretreatment demand storage at temperatures as low as, say, 4° C. Unduly long reaction time would be required if the reagents that had been kept in storage at such low temperatures were introduced directly into the sample tubes. It is therefore suggested that additional temporary storage vessels or reservoirs, not shown, be provided between the low temperature storage vessels of the reagents and the reagent supply nozzles 46. The capacities of the temporary storage vessels should be just about sufficient to hold only the amounts of the reagents to be subsequently charged into the sample tubes. The reagents will warm up approximately to room temperature while being kept in such temporary storage vessels.

Second Embodiment

FIGS. 18 through 22 show an alternate hydropneumatic circuit 163 to be employed with the cell treating apparatus 10 of FIGS. 1 and 2 in place of the circuit 63 of FIGS. 9 through 13. The alternate hydropneumatic circuit 163 features a pressurized air source 164a and a vacuum source 164b which in combination serves the functions of the pressurized air source 64 of the circuit 63. In practice, however, the pressurized air source 164a and vacuum source 164b may be combined into the form of a single air compressor, with the required conduits of the circuit 163 coupled to the outlet port and inlet port of the compressor as shown.

The vacuum source 164b communicates with one of the two ports of the temporary storage vessel 168 via three-way valves 190 and 192. The other port of the storage vessel 168 communicates with the supply-discharge nozzle 48 via a serial connection of another three-way valve 194 and a sample filter 196. A bypass conduit 180 extends between the two three-way valves 192 and 194 around the storage vessel 168. The vacuum source 164b also communicates directly with the waste reservoir 26 by way of a conduit 198. Additionally, the waste reservoir 26 communicates with a three-way valve 200. This valve 200 further communicates with the valve 190 on one hand and, on the other hand, with the pressurized air source 164a via an on-off valve 202 and also with the rinsing liquid reservoir 24 via another on-off valve 204.

Besides communicating with the on-off valve 202, the pressurized air source 164a communicates directly with the headspace within the rinsing liquid reservoir 24 by way of a conduit 206 and also with the headspace within each reagent bottle 20 by way of a conduit 208. The reagent bottles 20 communicate with the reagent supply nozzles 46 via on-off valves 210.

Operation of Second Embodiment

Figure 18:
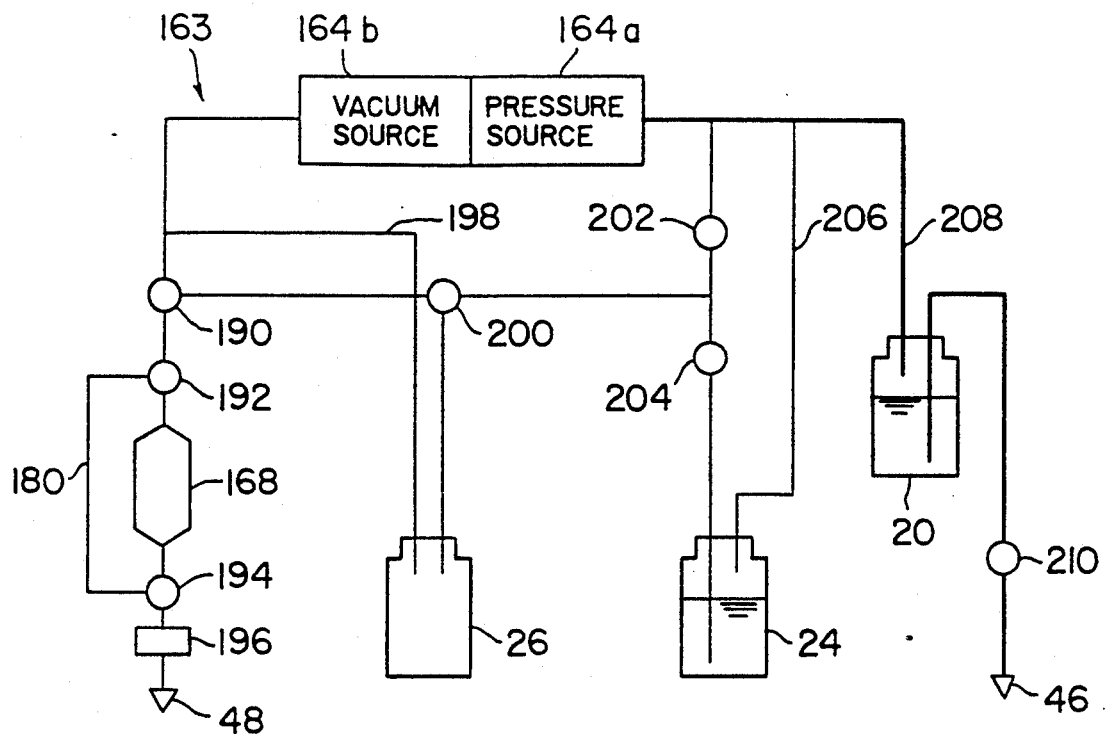
FIGS. 18 through 22 are a series of diagrams showing an alternate hydropneumatic circuit of the cell treating apparatus in various stages of cell treatment.

FIG. 18 shows the hydropneumatic circuit 163 conditioned for reagent supply into the sample tubes 16, FIG. 2, via the supply nozzles 46. The pressurized air source 164a is set into operation for pneumatically forcing the desired reagent into each sample tube via the on-off valve 210. The on-off valves 202 and 204 are closed during such reagent supply.

Figure 19:
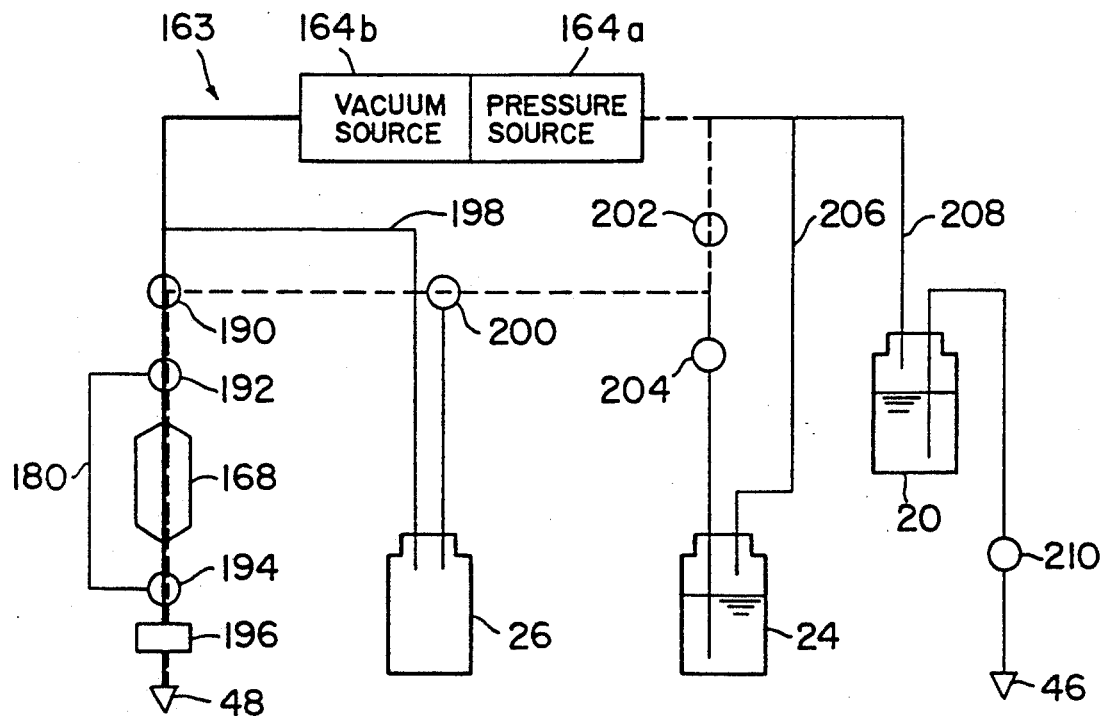
Figure 20:
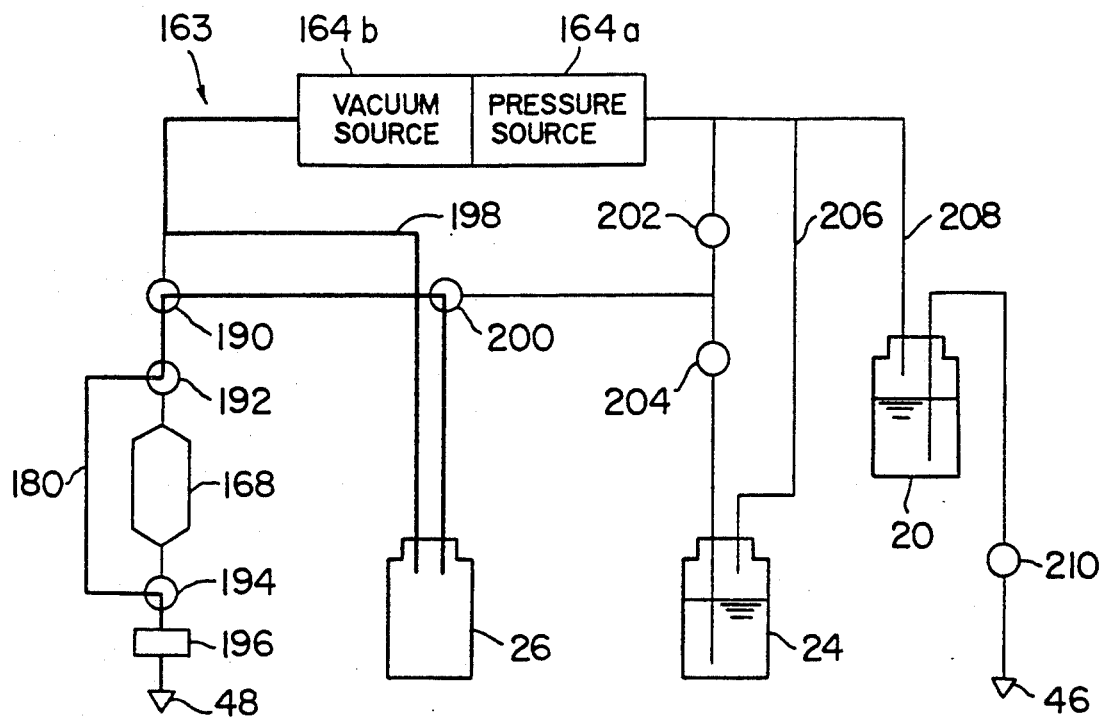

In FIG. 19 is shown how the samples and the reagent are subsequently intermingled by the hydropneumatic circuit 163. The vacuum source 164b is first set into operation for pneumatically drawing the sample-reagent mixture out of the sample tube 16 into the storage vessel 168, as indicated by the thick, solid line in FIG. 19. Then, with the three-way valve 190 positioned to communicate the pressurized air source 164a with the storage vessel 168, the pressurized air source is operated to force the sample-reagent mixture out of the storage vessel back into the sample tube, as indicated by the thick, broken line in FIG. 19. Such transfer of the sample-reagent mixture back and forth between sample tube and storage vessel may be repeated a required number of times for fully intermingling the sample and the reagent All the valves of the hydropneumatic circuit 163 are positioned as shown in FIG. 20 for discharging the unnecessary liquid top of the sample-reagent mixture from the sample tube following its centrifugal treatment which has been explained with reference to FIG. 2. The liquid tops will be withdrawn by suction from the sample tube and discharged into the waste reservoir 26 by flowing through the bypass conduit 180 around the storage vessel 168, as the vacuum source 164b is operated.

Figure 21:
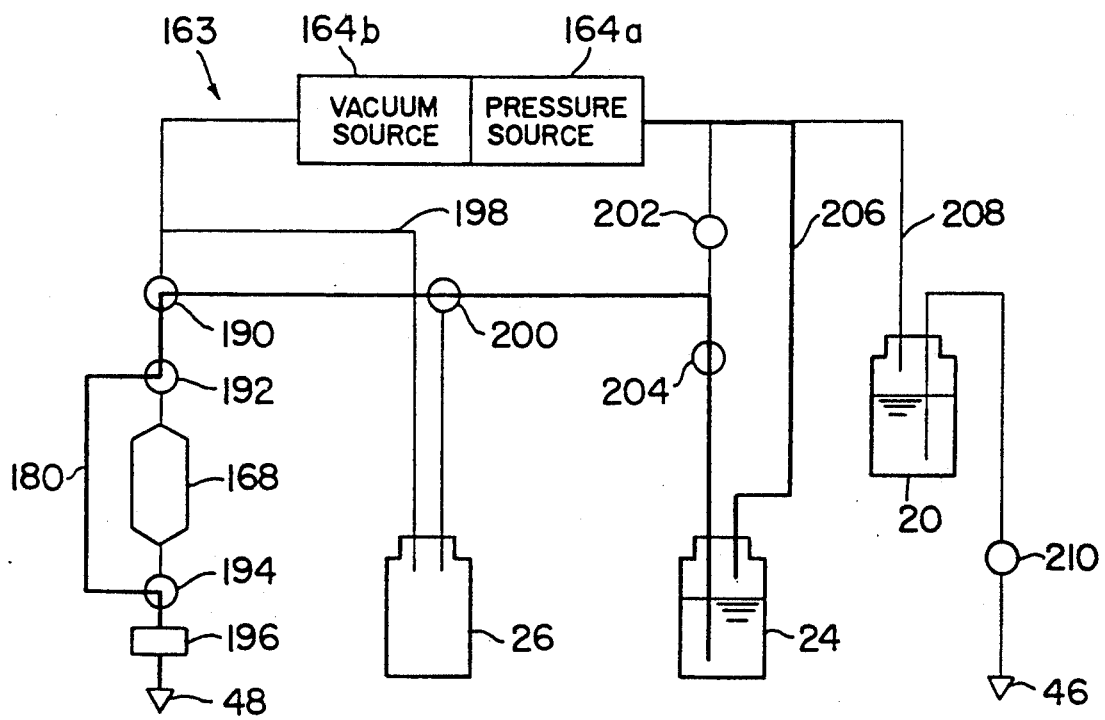

For rinsing, the pressurized air source 164a is operated after conditioning the hydropneumatic circuit 163 as shown in FIG. 21. Forced out of the reservoir 24, the rinsing liquid will flow through the bypass conduit 180 and supply-discharge nozzle 48 and will be discharged through the discharge port 84 shown in FIG. 8.

Preferably, at the same time with such rinsing of the inside of the supply-discharge nozzle 48, a rinsing liquid is sprayed on its outside, too, by means not shown in the drawings. The rinsing liquid so sprayed is collected by a tray or pan, not shown, and directed by suitable piping, also not shown, into the waste reservoir 26.

Figure 22:
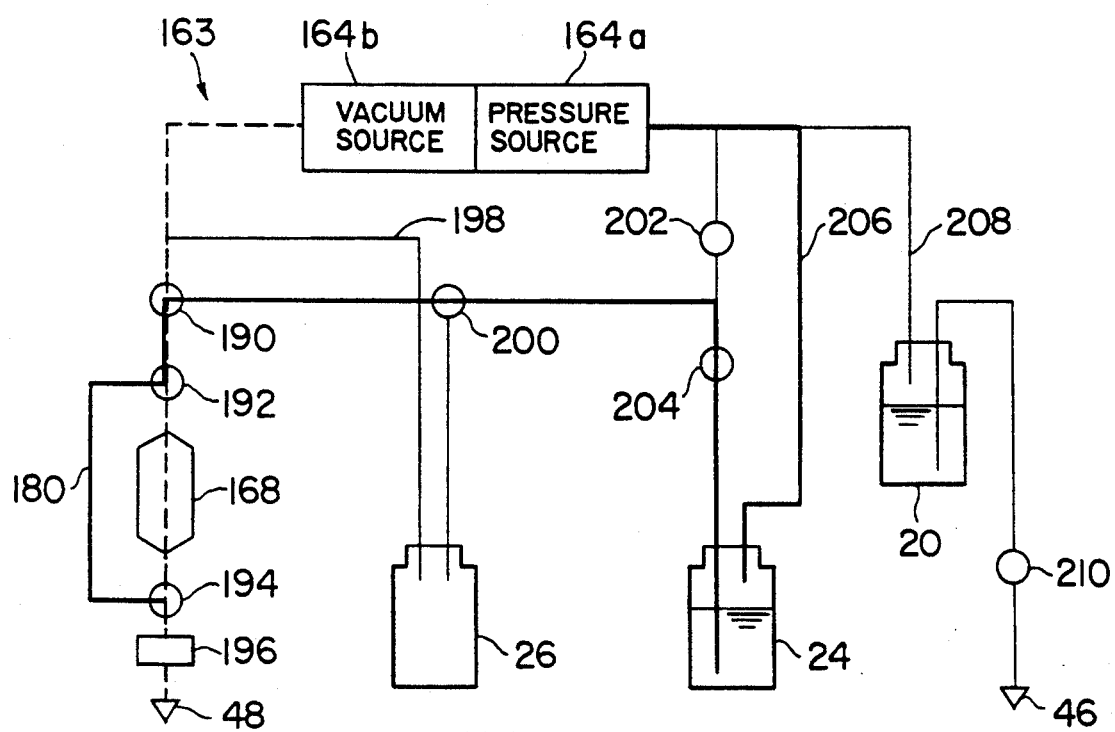

For sample filtration the hydropneumatic circuit 163 is conditioned as indicated by the thick, broken line in FIG. 22. The sample will be transferred by suction from sample tube 16 to storage vessel 168 as the vacuum pump 33 is operated. Flowing through the filter 196, the sample will be freed from undesired solids that may have been contained therein.

Then, after revolving the sample carrier 14 with the positioning motor 40 through an angle required to bring the hole 42 into alignment with the discharge port 84, FIG. 8, the valves of the hydropneumatic circuit 163 are positioned as indicated by the thick, solid lines in FIG. 22. Then the pressurized air source 164a is operated to cause the rinsing liquid to flow from its reservoir 24 into the discharge port 84 through the bypass conduit 180 and sample filter 196. So backwashed, the sample filter 196 will be cleaned free of the solids that have been collected from the sample. Then the sample carrier 14 is revolved again to move the required sample tube back into alignment with the supply-discharge nozzle 48. Then the required valves of the hydropneumatic circuit 163 is actuated again to return the filtered sample from storage vessel 168 into sample tube 16 under the force of the pressurized air from the source 164a.

Third Embodiment

Figure 23:
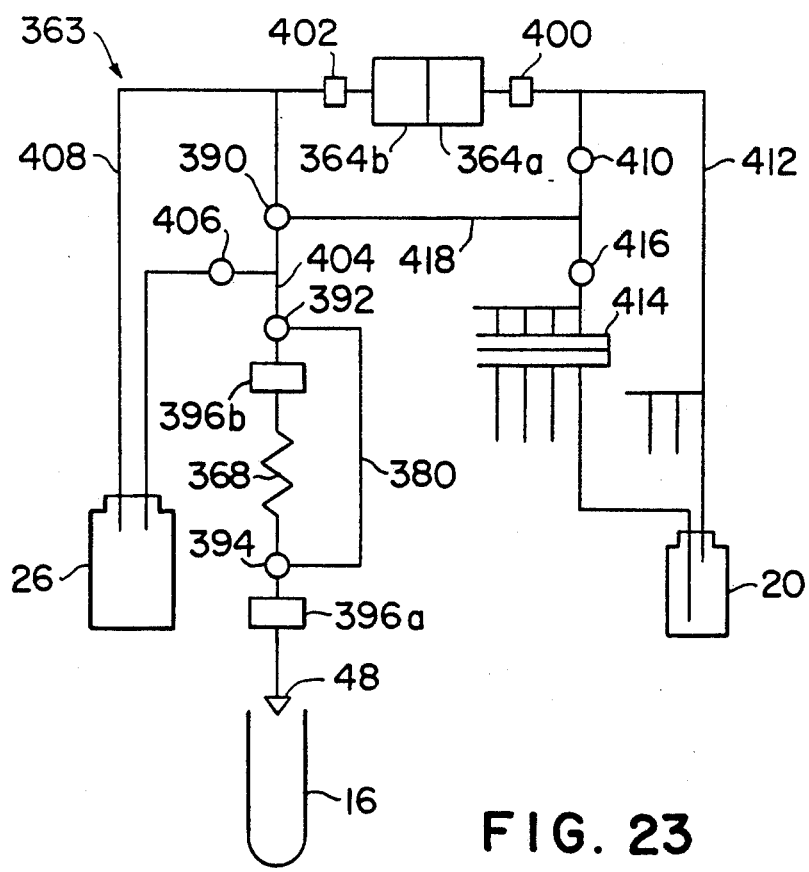
FIG. 23 is a diagram of another alternate hydropneumatic circuit according to this invention.

FIG. 23 shows another alternate hydropneumatic circuit 363 which dispenses with the reagent supply nozzles of the foregoing embodiments. This second alternate hydropneumatic circuit 363 also employs a pressurized air source 364a and a vacuum source 364b. However, in this circuit 363, the output pressure of the pressurized air source 364a should be significantly more in absolute value than that of the vacuum source 364b. Typically, the output pressure of the pressurized air source 364a may be +380 millimeters of mercury (mmHg), and the negative pressure developed by the vacuum source 364b may be approximately −200 mmHg.

As has been mentioned in connection with the hydropneumatic circuit 163 of FIGS. 18 through 22, the pressurized air source 364a and vacuum source 364b may be combined into a single air compressor, with the required conduits of the circuit 363 coupled to the outlet port and inlet port of the compressor as shown. Also, in this case, pressure regulator valves should be provided as at 400 and 402 in order to make the positive output pressure of the compressor significantly more than the absolute value of the negative pressure drawn by the compressor.

The temporary storage vessel 368 of this hydropneumatic circuit 363 is shown as a pipe of relatively small diameter, but with a length such that the resulting pipe capacity is enough to accommodate the complete sample liquid within each sample tube 16. The storage vessel 368 has one of its two inlet-outlet ports in communication with the supply-discharge nozzle 48 via a three-way valve 394 and a sample filter 396a of relatively coarse mesh. The other inlet-outlet port of the storage vessel 368 communicates with the vacuum source 364b via a serial connection of another sample filter 396b of relatively fine mesh, two three-way valves 390 and 392, and the pressure regulator valve 402. The coarse mesh sample filter 396a should be capable of arresting solids of, say, 40 micrometers and more, and the fine mesh sample filter 396b those of, say, one micrometer and more. A bypass conduit 380 extends between the three-way valves 394 and 392, bypassing the storage vessel 368 and fine mesh sample filter 396b.

A conduit 404 extending between the three-way valves 390 and 392 also communicates with the hermetically closed waste reservoir 26 via an on-off valve 406. Another conduit 408 communicates with of the waste reservoir 26 with the vacuum source 364b via the pressure regulator valve 402.

The three-way valve 390 also communicates with the pressurized air source 364a via an on-off valve 410 and the pressure regulator valve 400. A conduit 412 communicates the headspaces of all the reagent bottles or containers 20, one seen in FIG. 23, with the pressurized air source 364a the pressure regulator valve 400.

A rotary selector valve is provided at 414 for selective delivery of different reagents, as well as a rinsing liquid, from their containers 20 to the supply-discharge nozzle 48. The rotary selector valve 414 communicates separately with all the reagent and rinsing liquid containers 20 and, via an on-off valve 416, with the conduit 418 extending between three-way valve 390 and on-off valve 410.

Operation of Third Embodiment

Figure 24:
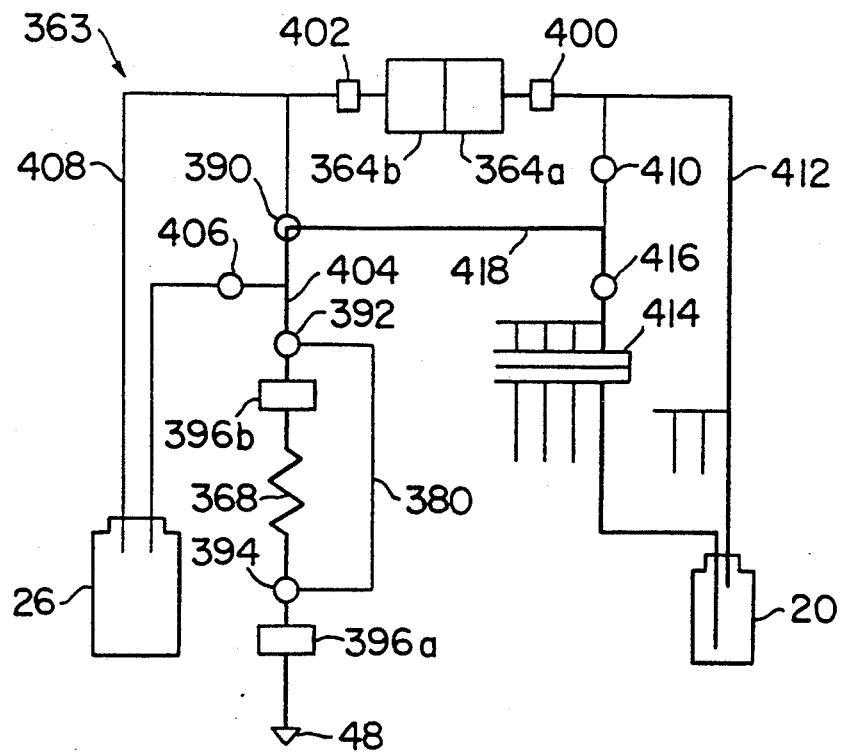
FIGS. 24 through 28 are diagrams similar to FIG. 23 but showing the hydropneumatic circuit in various stages of cell treatment.

FIG. 24 is explanatory of how a reagent is introduced from any selected reagent container 20 into any selected sample tube 16 in the hydropneumatic circuit 363 of the foregoing construction. The on-off valve 410 is closed. Therefore, with the operation of the pressurized air source 364a, air will be forced into all the reagent containers 20, driving out the reagents therefrom. However, only the reagent from the selected reagent container will pass through the rotary selector valve 414 The selected reagent will drop into the sample tube 16 after flowing through the on-off valve 416, three-way valves 390 and 392, fine mesh sample filter 396b, temporary storage vessel 368, three-way valve 394, and coarse mesh sample filter 396a. The reagent introduction into the sample tube is discontinued by closing the on-off valve 416.

Figure 25:
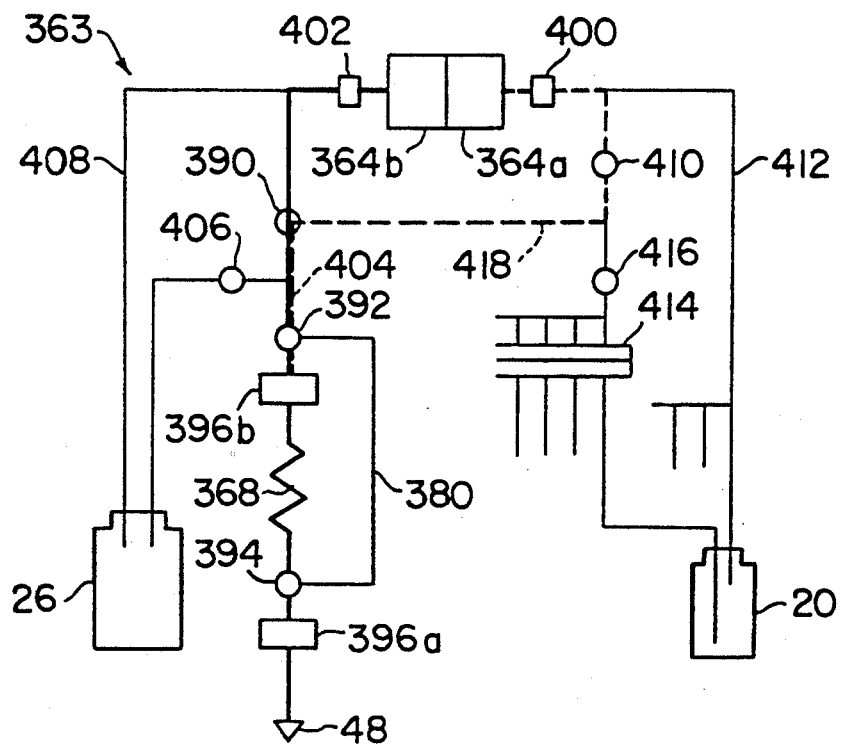

Then, for intermingling the sample and the reagent, the supply-discharge nozzle 48 is inserted fully in the sample tube 16, to the lowermost position $Z_2$ of FIG. 5. Then the hydropneumatic circuit 363 is conditioned to cause fluid flow along the path indicated by the thick, solid line in FIG. 25. Then the vacuum source 364b is set into operation.

Thereupon the sample-reagent mixture will be drawn by suction from sample tube 16 into temporary storage vessel 368 via the supply-discharge nozzle 48, coarse mesh sample filter 396a and three-way valve 394. The vacuum source 364b is set out of operation upon lapse of a prescribed time, at the end of which the sample-reagent mixture has been transferred to the temporary storage vessel 368 either wholly or in part. Then, with the three-way valve 390 actuated to place the storage vessel 368 in communication with the pressurized air source 364a via the on-off valve 410, the pressurized air source is set into operation. Then the sample-reagent mixture will be pneumatically forced out of the storage vessel 368 back into the sample tube 16. Such transfer of the sample-reagent mixture back and forth between sample tube 16 and storage vessel 368 may be repeated until the desired reaction between the sample and the reagent is completed.

As required, means may be provided for heating and cooling the temporary storage vessel 368. Such means are intended for causing the reaction between sample and reagent to take place within the storage vessel under specified temperature conditions.

The noted repeated transfer of the sample-reagent mixture between sample tube 16 and storage vessel 368 serves the additional purpose of breaking up coherent cell aggregates that may be contained in the sample liquid. Such aggregates will separate into individual cells by being forced back and forth through the coarse mesh sample filter 396a. Cell aggregates will more readily break up into individual cells by vibrating the sample tube 48 and/or the coarse mesh sample filter 396a at an ultrasonic frequency.

As a possible alternative to the sample filter 396a, there may be employed a serial arrangement of two or more filters of different mesh sizes. For example, three filters that pass solids of up to one millimeter, 200 micrometers, and 40 micrometers in size, respectively, may be serially provided in that order from the supply-discharge nozzle 48 toward the three-way valve 394. Cell aggregates will then gradually break up into smaller masses and finally into individual cells without excessively clogging the filters.

For backwashing the coarse mesh sample filter 396a, the supply-discharge nozzle 48 is raised to the uppermost position $Z_0$, FIG. 7, and so withdrawn from the sample tube 16, with the sample-reagent mixture held contained in the storage vessel 368. Then the sample carrier 14, FIG. 2, is revolved to the required angular position to bring its hole 42, FIG. 3, into register with the supply-discharge nozzle 48.

Figure 26:
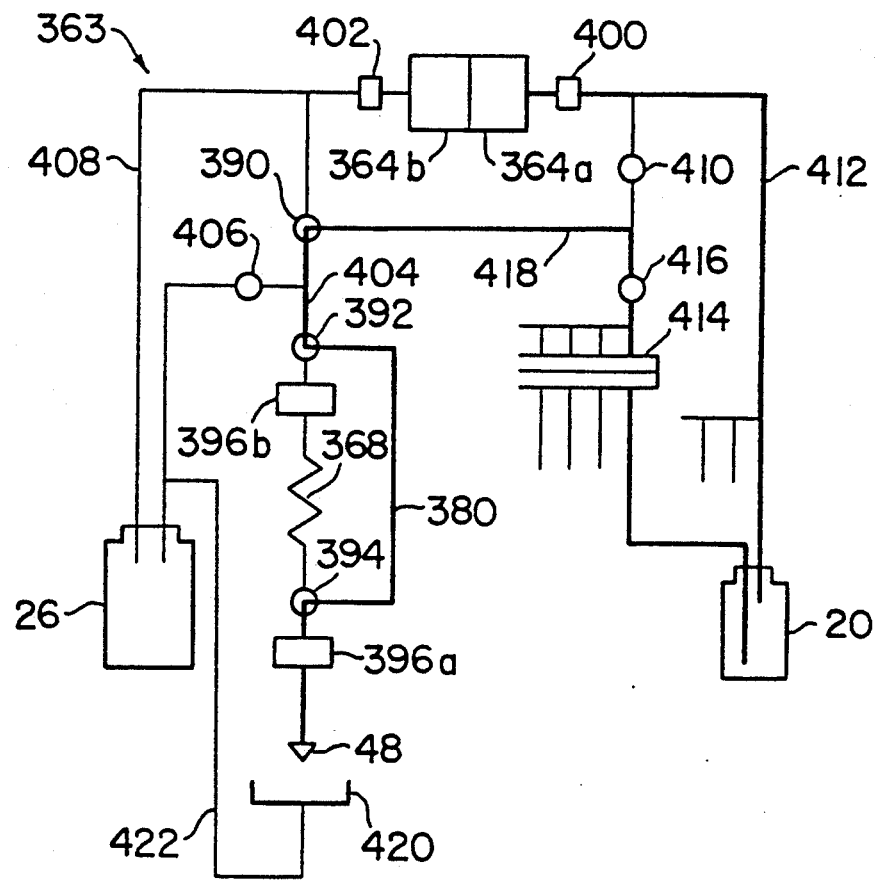

FIG. 26 shows the supply-discharge nozzle 48 thus placed in open communication with an underlying discharge pan 420 and thence with the waste reservoir 26 by way of a conduit 422. Then the valves of the circuit 363 is actuated to cause fluid flow along the path indicated by the thick line in FIG. 26. The rotary selector valve 414 is positioned to communicate that one of the containers 20 which contains the rinsing liquid. Then the pressurized air source 364a is set into operation. Forced out of its container 20, the rinsing liquid will flow into the waste reservoir 26 through the rotary selector valve 141, on-off valve 416, conduit 418, three-way valves 390 and 392, bypass conduit 380, three-way valve 394, coarse mesh sample filter 396a, supply-discharge nozzle 48, and discharge pan 420.

As has been stated, the pressure under which the coarse mesh sample filter 396a is backwashed as above is much higher than the pressure under which the sample-reagent mixture flowed through the filter from the sample tube 16 toward the storage vessel 368. The undesired cell aggregates and other solids that have been captured by the coarse mesh sample filter 396a will be effectively liberated therefrom by the rinsing liquid and flow therewith into the waste reservoir 26. The supply-discharge nozzle 48 will be rinsed at the same time.

Figure 27:
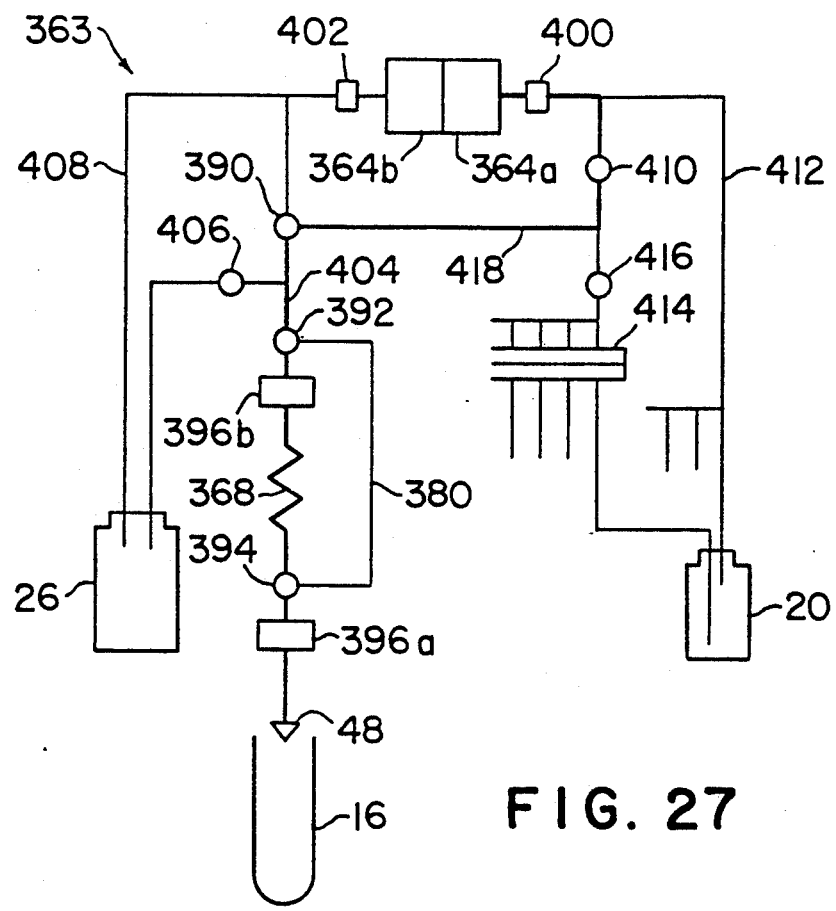

Then the hydropneumatic circuit 363 is conditioned as shown in FIG. 27, and the pressurized air source 364a is operated to return the sample-reagent mixture back into the sample tube 16 along the path indicated by the thick line in this diagram.

Such return of the sample-reagent mixture into the sample tube 16 through the sample filter 396a may be undesirable in some instances because of the possible coagulation of the cells and the consequent clogging of the filter. In order to preclude this possibility, the temporary storage vessel 368 is communicated with the supply-discharge nozzle 48 by an additional conduit, not shown, bypassing the three-way valve 394 and sample filter 396a. An on-off valve, also not shown, may be provided on this additional bypass conduit for the on-off control of direct communication between storage vessel 368 and supply-discharge nozzle 48.

Figure 28:
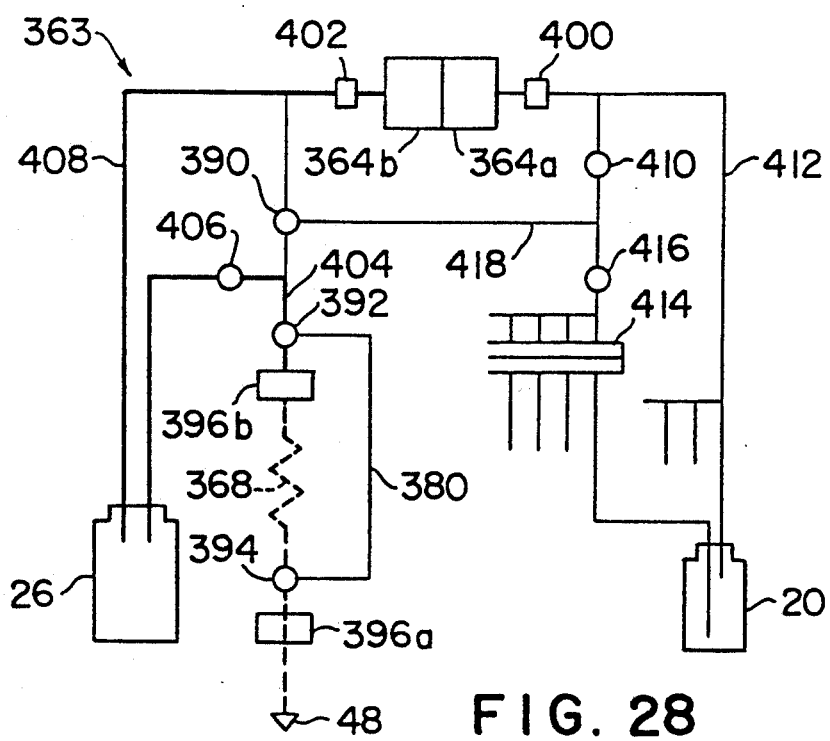

Then the hydropneumatic circuit 363 is conditioned as shown in FIG. 28. Then, after inserting the supply-discharge nozzle 48 fully in the sample tube 16, the vacuum source 364b is set into operation. The vacuum source 364b will create a partial vacuum first in the waste reservoir 26 and then in the storage vessel 368, as indicated by the thick, solid line in FIG. 28. The sample-reagent mixture will then be drawn by suction from sample tube 16 into storage vessel 368 along the path indicated by the thick, broken line in the same diagram. Further the liquid component of the sample-reagent mixture will be drawn from storage vessel 368 into waste reservoir 26 via the fine mesh sample filter 396b.

Alternatively, the above discharge of the liquid component of the sample-reagent mixture into the waste reservoir 26 may be performed immediately after the filter backwashing operation of FIG. 26, that is, while the sample-reagent mixture is still contained in the storage vessel 368. The step of FIG. 27 will then be unnecessary.

The sample-reagent mixture being drawn by suction from sample tube 16 into storage vessel 368 along the thick, broken line path of FIG. 28 as above may still contain cell aggregates. Such cell aggregates will be arrested by the coarse mesh sample filter 396a. The fine mesh sample filter 396a, on the other hand, will capture individual cells suitable for flow cytometry, permitting only the liquid component of the sample-reagent mixture to flow therethrough toward the waste reservoir 26.

Then the circuit 363 is again conditioned as shown in FIG. 24, only with the rotary selector valve 414 reactuated to communicate the next required reagent container 20 with the conduit 418. Then the pressurized air source 364a is set into operation. The reagent from the selected reagent container 20 will flow through the path indicated by the thick line in this diagram and will be dropped into the sample tube from the supply-discharge nozzle 48. It will be seen that the fine mesh sample filter 396b is backwashed by this reagent flow. The sample cells that have been caught by this filter 396b will therefore be liberated therefrom and will flow with the reagent back into the sample tube. The sample cells are returned to the sample tube through the aforesaid bypass conduit, not shown, if there is the danger of cell coagulation. The on-off valve 416 is closed to terminate the reagent flow from its container 20.

Similar operations may be repeated until the full pretreatment of the sample cells is completed. Then, with the circuit 363 conditioned as shown in FIG. 27, the pressurized air source 364a is operated to return the pretreated cells into the sample tube 16. The sample tubes containing the pretreated cells are then transferred to separate apparatus for flow cytometry, either manually or by automatic means.

In this embodiment, too, only one supply-discharge nozzle 48 may be provided for use with one or more sample tubes in the simplest form of this invention. However, as has been mentioned in connection with the first disclosed hydropneumatic circuit 63, the dropping of a reagent into successive sample tubes from one the same supply-discharge nozzle may be undesirable because of the differences in reaction time among the samples. There may therefore be provided as many supply-discharge nozzles 48, and as many temporary storage vessels 368 capable of communication one with each such nozzle, as there are sample tubes 16 to be processed simultaneously. All the samples within the sample tubes will then be treated concurrently.

Not only reaction time but also reaction temperatures need strict control for cell pretreatment for flow cytology. If only one supply-discharge nozzle is employed, temperature control may be made through a holder, not shown, of the sample tube. However, if a plurality of supply-discharge nozzles are employed, as many temporary storage vessels are required. The complete temporarily storage vessels may be housed in suitable constant temperature vessels in such cases.

Also, in this embodiment, too, additional temporary storage vessels may be provided for temporarily storing desired amounts of some reagents that have been stored at reduced temperatures, before they are caused to flow from their low temperature containers to the supply-discharge nozzle or nozzles. The reagents will warm up to a temperature suitable for reaction with the sample cells while being kept in such vessels.

Additional modifications, alterations and adaptations of the present invention will suggest themselves to those skilled in the art without departing from the scope of the invention as expressed in the following claims.

What is claimed is:

1. An apparatus for treating cells preparatory to a cytological study, said apparatus comprising:
   (a) sample containers for containing a sample liquid containing cells to be treated;
   (b) reagent containers for containing one or more reagents to be added to the sample liquid;
   (c) a rinsing liquid container for container a rinsing liquid;
   (d) pneumatic energy source means for developing pneumatic energy;
   (e) a horizontal rotary sample carrier of a substantially disk shape rotatable about a vertical axis,
   (f) a sample rack of a substantially arcuate elongated shape mounted on said sample carrier along a peripheral edge thereof, said sample rack being pivoted at two ends thereof to the sample carrier so as to be swingable radial outwardly of the sample carrier under centrifugal force when the carrier is rotated about said vertical axis, said sample rack having therealong a row of holes for receiving said sample containers;
   (g) drive means for imparting rotation about said vertical axis to the sample carrier to centrifuge the sample containers received in the holes of said sample rack;

(h) constant temperature vessels of substantially arcuate elongated shape, said vessels having thermostatic means for maintaining a constant desired temperature and being provided horizontally under said sample carrier, said vessels being disposed in series in annular arrangement below a peripheral edge of the sample carrier, each of said vessels being movable vertically relative to the sample carrier to a position in which the sample containers carried by the sample rack are inserted into one of the vessels for application of a desired temperature to the sample containers;

(i) a row of reagent supply nozzles disposed above the sample carrier along a peripheral edge thereof for simultaneously dropping the reagents into the sample containers on the sample rack to form sample-reagent mixtures in the sample containers;

(j) a selector valve for selectively supplying the reagents and the rinsing liquid from said reagent containers and said rinsing liquid container into the sample containers;

(k) a supply-discharge nozzle capable of communication with said selector valve and the pneumatic energy source means and movable into and out of the sample containers for introducing any of the one or more reagents or the rinsing liquid into the sample containers, and for withdrawing the sample-reagent mixtures or the rinsing liquid from the sample containers, under the force of the pneumatic energy;

(l) positioning means coupled to said sample carrier for angularly indexing the carrier about the vertical axis thereof so as to cause the sample containers on the sample rack to take positions in vertical alignment with said reagent supply nozzles, said supply-discharge nozzle and said constant-temperature vessels;

(m) a temporary storage vessel capable of communication with the supply-discharge nozzle; and (n) valve means for controlling the communication of the supply-discharge nozzle with the selector valve and the pneumatic energy source means and the temporary storage vessel to intimately intermingle the sample liquid and the reagents by causing the flow of the sample-reagent mixtures back and forth between the sample containers and the temporary storage vessel, and to rinse the nozzle means and the temporary storage with the rinsing liquid.

2. The cell treating apparatus of claim 1, wherein each of the sample containers has an open top, and wherein the supply-discharge nozzle has a flange formed thereon for hermetically closing the open top of one of the sample containers when fully inserted therein.

3. The cell treating apparatus of claim 1, wherein the pneumatic energy source means comprises means for developing both positive and negative pneumatic pressures.

4. The cell treating apparatus of claim 3, wherein the positive pneumatic pressure is greater in absolute value than the negative pneumatic pressure.

5. The cell treating apparatus of claim 1, further comprising:

(a) a first sample filter disposed between the temporary storage vessel and the supply-discharge nozzle for breaking up coherent cell aggregates into individual cells; and (b) a second sample filter of finger mesh than the first sample filter, the second sample filter being disposed between the temporary storage vessel and the pneumatic energy source means for arresting the individual cells.

* * * * *